(12) United States Patent
Battiston

(10) Patent No.: US 7,671,511 B2
(45) Date of Patent: Mar. 2, 2010

(54) SYSTEM FOR OSCILLATING A MICROMECHANICAL CANTILEVER

(75) Inventor: Felice Mauro Battiston, Muttenz (CH)

(73) Assignee: Concentris GmbH, Basel (CH)

( * ) Notice: Subject to any disclaimer, the term of this patent is extended or adjusted under 35 U.S.C. 154(b) by 65 days.

(21) Appl. No.: 11/954,126

(22) Filed: Dec. 11, 2007

(65) Prior Publication Data
US 2008/0136291 A1 Jun. 12, 2008

(30) Foreign Application Priority Data
Dec. 12, 2006 (DE) .................. 10 2006 058 933

(51) Int. Cl.
*H01L 41/09* (2006.01)
(52) U.S. Cl. .................. 310/316.01; 310/317; 310/340; 310/344; 310/348; 310/353
(58) Field of Classification Search ............ 310/316.01, 310/316.02, 317–319, 338, 340, 344, 348, 310/349, 352, 353
See application file for complete search history.

(56) References Cited

U.S. PATENT DOCUMENTS

| | | | | |
|---|---|---|---|---|
| 4,549,427 | A | | 10/1985 | Kolesar, Jr. |
| 4,626,730 | A | * | 12/1986 | Hubbard, Jr. ............... 310/326 |
| 5,198,716 | A | * | 3/1993 | Godshall et al. ............ 310/349 |
| 6,583,412 | B2 | * | 6/2003 | Williams .................... 250/306 |
| 7,002,436 | B2 | * | 2/2006 | Ma et al. .................... 333/186 |
| 7,389,679 | B2 | * | 6/2008 | Battiston et al. ........... 73/61.79 |
| 2005/0199047 | A1 | * | 9/2005 | Adams et al. .................. 73/105 |

FOREIGN PATENT DOCUMENTS

| | | | |
|---|---|---|---|
| JP | 2003-224447 | * | 8/2003 |
| WO | 98/50773 | | 11/1998 |
| WO | 01/33226 | | 5/2001 |

OTHER PUBLICATIONS

Battiston et al.; "Sensors and Actuators B77"; 2001, pp. 122-131. (Previously listed on IDS submitted on Dec. 11, 2007).
Braun et al.; "Phys. Rev. E 72 01907"; 2005. (Previously listed on IDS submitted on Dec. 11, 2007).
Battiston et al.; "Sensors and Actuators B77"; 2001, pp. 122-131.
Braun et al.; "Phys. Rev. E 72 01907"; 2005.

* cited by examiner

*Primary Examiner*—Thomas M Dougherty
(74) *Attorney, Agent, or Firm*—Renner, Otto, Boisselle & Sklar, LLP

(57) ABSTRACT

This invention relates to a system for exciting oscillations of micromechanical cantilever sensors and for measuring and evaluating the corresponding oscillations. Such sensors can e.g. be used to detect chemical substances, biomolecules, microorganisms or viruses, or to analyze surface-related phenomena and processes such as conformational changes or phase transitions in thin layers, or to measure physical properties of their surrounding, such as viscoelastic properties of liquids. In the so-called dynamic operation mode, cantilever oscillations are excited and the frequency shift of the ground frequency and/or of one or some higher harmonics, occurring because of a process taking place at the cantilever surface, are measured. In the so-called static mode, the deflection of the cantilever is determined. The setup described in this invention allows measurements in gases as well as liquids. It is characterized by an efficient transfer of the oscillation from a piezoelectric driver element to the cantilever over a wide frequency range. This is achieved through a sophisticated combination of a solid support structure, oscillation driver and insulators.

17 Claims, 6 Drawing Sheets

SYSTEM FOR OSCILLATING A MICROMECHANICAL CANTILEVER

FIELD OF THE INVENTION

Figure 1:
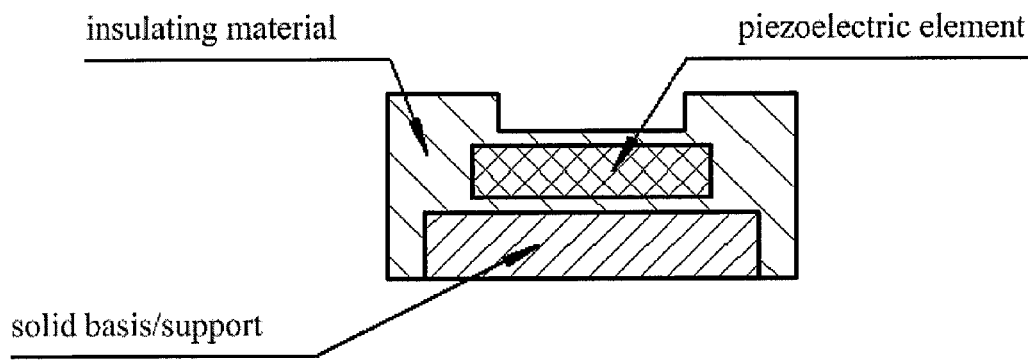

The present invention relates to a system for exciting oscillations of a micromechanical cantilever sensor and a method for operating this apparatus. Chemically coated (functionalized), micro-fabricated cantilever sensors are characterized by their high sensitivity and are used e.g. to detect chemical substances, biomolecules, viruses, bacteria or to analyze surface-related phenomena. Two operation modes are commonly used: In the "static" mode, the bending of the cantilever in response to a force (e.g. surface stress) is measured. In the "dynamic" mode, the resonance frequency (eigenfrequency) and/or higher harmonics are measured. Small frequency shifts are used to determine e.g. the change in mass load on the cantilever or changes in the properties of either the cantilever surface layer or the surrounding medium. In order to operate a cantilever sensor in dynamic mode, it is necessary to have a means to excite the cantilever oscillation. Especially when measuring in liquids, the strong damping of the oscillation can make an exact determination of the resonance frequency difficult. The present invention addresses this difficulty with a highly efficient excitation of cantilevers over a large frequency range. It can be used in gaseous as well as liquid environments. This device is especially well suited for the read-out of cantilever oscillations with optical methods, e.g. beam deflection, interferometry, but may also be used in combination with other detection means without any difficulty.

DESCRIPTION OF THE PRIOR ART

When used for applications in the fields of biosensors or chemical analysis, cantilevers are typically manufactured using micro-fabrication techniques.

They are designed as cantilevered springs fixed to a solid support at one end and able to move freely at the other end. This cantilever is typically coated—or functionalized—with a specific receptor molecule able to selectively bind a certain target substance. This sensor is then typically brought into contact with the analyte liquid or gas. If molecules of the target substance are present in the sample, they chemically bind to or interact with the receptor molecule on the sensor. This leads to a change of the surface stress on the cantilever and at the same time increases the mass load of the cantilever. While surface stress causes a small mechanical bending (deflection) of the cantilever, an increase in mass load typically decreases the resonance frequency of the cantilever. Both effects—the minimal deflection as well as changes in the oscillation properties—can be measured with high accuracy and used as indicator for the quantity to be measured.

Generally speaking, a mechanical change in the properties or behavior of the cantilever serves as a means of detection. The high sensitivity of cantilever sensors as well as the combination of two complementary measurement modes (static and dynamic) are particular advantages, which differentiate cantilever sensors from many other methods.

Applications in the field of biology usually require highly specific interactions, e.g. antigen-antibody interaction or hybridization of complementary DNA strands. These applications are well established in the literature, as is illustrated by the following examples:

In the PCT patent application WO 98/50773 (1997), D. Charych et al. describe the detection of (bio-) molecules based on the "key-lock-principle", i.e. by immobilizing specific binding partners of the target substance to be detected with the cantilever.

In addition, in the PCT patent application WO 0133226, M. K. Bailer et al. describe the use of similarly functionalized reference cantilevers within a cantilever array under the title "Cantilever and Transducers". This differential measurement method, where deflections of different cantilevers within an array are compared to each other, allows more reliable and stable measurement by compensating undesired effects, e.g. variations in sample temperature, by subtracting a reference signal.

Both patent specifications relate exclusively to the static operation mode. Measurements in the dynamic mode were predominantly used for the analysis of gaseous substances, because the strong damping of the oscillation in liquids leads to a low quality factor and makes determination or tracking of the resonance frequency difficult with existing assemblies. Additionally, many liquids (e.g. all buffer solutions used for biological measurements) contain ions and are therefore electroconductive. Therefore, especially the oscillation excitation by means of a piezoelectric element requires an electrical isolation.

In U.S. Pat. No. 4,549,427, E. S. Kolesar describes the detection of nerve agents by means of chemically coated cantilever sensors in dynamic operation mode. Here, the natural frequency of the cantilever is determined by subjecting the cantilever to an initial tension by applying an electrical voltage. When the voltage is switched off, the cantilever rebounds and starts to oscillate. Its decaying oscillation is measured. This apparatus is suitable for the analysis of gases, but not liquids. In addition, only the fundamental frequency of the cantilever or cantilevers can be determined.

In *Sensors and Actuators B* 77 (2001), 122-131, Battiston et al. describe the use of a cantilever array coated with different polymers as an "electronic nose". Here, cantilevers are mechanically driven at their natural resonance frequency using a piezoelectric element. The dynamic mode signal (frequency shift) is determined by means of a PLL (phase locked loop). By low-pass filtering this signal, the static mode signal can be determined simultaneously. The setup used to drive the cantilever cannot be used in liquids, because there is no electrical isolation. Furthermore it is not optimized for optimal efficiency of the transfer of the oscillation energy to the cantilever, mainly because all measurements occur in a gaseous environment. Finally, the cantilever is glued to the setup, which makes replacement difficult or impossible.

Measurements in the dynamic mode at higher harmonics of cantilevers are described by Braun et al. in *Phys. Rev. E* 72 031907 (2005). Here, the cantilever array is directly attached to a piezoelectric element which drives the cantilever oscillation. The piezoelectric element is located inside the liquid, which on one hand makes electrical isolation necessary and on the other hand leads to a strong coupling of the oscillation driver to the liquid and thereby the entire measurement setup. This may lead to reflections and interferences with resonance frequencies of the setup which reflections/interferences may adversely affect measurements. Furthermore, an easy to handle means for exchanging the cantilever arrays is missing.

In all of the above cases, the cantilever oscillation can be read-out optically, e.g. by means of deflection of a laser beam (beam deflection), interferometrically, piezoelectrically, piezoresistively, capacitively or by employing any other known method.

SUMMARY OF THE INVENTION

The present invention concerns a setup for exciting oscillations of micromechanical cantilever sensors in a dynamic operation mode. The setup combines a highly efficient oscillation excitation with the possibility to measure in gases and fluids over a large range of frequencies. In contrast to the state of the art, the piezoelectric element used to excite the oscillation is not in direct contact with the cantilever but rather integrated into a sandwich-like structure, which may be part of holder. This enables easy exchange of the cantilever or cantilever array.

In a typical embodiment of the setup for oscillation excitation, the piezoelectric element is fully surrounded by an electrically insulating material, the "insulator" which insulates the piezoelectric element both from the liquid and electrically. In order to achieve a high efficiency in the transfer of the oscillation energy to the cantilever, the insulator on one side of the piezoelectric element is kept as thin as possible, typically 0.2 mm, and its surface, on which the cantilever support structure is mounted, is flat and smooth to ensure a good mechanical contact over its entire area. On the other, opposite side, the piezoelectric element is firmly fixed to a solid basis. If a cantilever is mounted on the thin side of the insulator, the efficiency of the energy transfer is optimal because the solid basis only absorbs oscillation energy to a very low extent and the flat, smooth surface allows optimum mechanical contact between the oscillation driver and the cantilever. This arrangement enhances the efficiency of energy transfer and compensates the losses due to damping in liquids, thus enabling dynamic mode measurements in liquids.

The complete sealing of the oscillator and wires allows this device to be used in many environments such as gases and liquids or even harsh environments, such as e.g. plasma.

Another advantage of the above setup is that the high efficiency coupling allows a wide range of driving frequencies to be transferred to the cantilever, typically starting at a few kHz and ranging up to several MHz. This e.g. enables to measure at higher harmonic frequencies of the cantilever, to drive cantilever arrays containing cantilevers with different natural frequencies, or to determine the oscillation amplitude of the cantilever over a wide frequency range.

In a typical embodiment of the setup, the cantilever or cantilever array is fixed with its support structure to the thin insulator layer. This can be accomplished by means of glue or—if exchangeability is required—by means of a clamping arrangement or screw, which presses the cantilever support structure against the insulator in order to obtain a good and firm mechanical contact.

In a special embodiment, the piezoelectric element isolated according to this invention is part of a holder (or cartridge), which enables easy handling of the cantilever. This holder may be specifically designed for a measurement cell as described in German patent application DE 10 2004 046 685. Typically the side with the thick part of the insulator will be firmly attached to the holder. The cantilever or cantilever array is usually fixed to or mounted on the opposite side with the thin insulator through its support structure in one of the ways described above.

In a further special embodiment, the material used as the basis for the piezoelectric element is a hard metal, e.g. titanium, and the insulator between the piezoelectric element and the metal support is a ceramic plate. The piezoelectric element is firmly fixed to the ceramic plate and the ceramic plate is firmly attached to the metal support, e.g. with glue. The opposite side of the piezoelectric element is covered with a thin isolating layer, typically with a thickness of 0.2 mm or less, which offers a flat and smooth contact area for the cantilever support structure. In addition, the sides of this arrangement are isolated electrically and against intrusion of liquids.

In a further special embodiment, the isolation on the sides and the thin insulating layer on top of the piezoelectric element are designed as a monolithic block. The piezoelectric element which is firmly fixed to the solid basis is embedded in this monolithic block. Additionally, the monolithic block may contain ducts for the contact wires needed for contacting the piezoelectric element.

In a special arrangement, the monolithic block is made of a biocompatible material or plastic, e.g. polyetheretherketone (PEEK).

Another embodiment is characterized by two ceramic pads fixed to the upper and lower side of the piezoelectric element. One of these pads is fixed to the support, while the other is in contact with the thin insulator layer. On one side, the ceramic pad serves as spacer between the piezoelectric element and the support or the thin insulation layer, respectively. On the other side, the wires contacting the piezoelectric element may be placed inside corresponding notches in the ceramic pads. The high hardness of the ceramic pads ensures an efficient transfer of the oscillation.

Typically, the piezoelectric element is electrically connected to an electronics circuit driving the oscillation by applying an alternating voltage. This leads to an oscillation of the piezoelectric element and consequently to an oscillation of the cantilever or cantilevers.

If desired, observing the amplitude of the cantilever oscillation signal at various excitation frequencies (e.g. by means of a frequency sweep over a defined range) allows to determine the resonance (ground) frequency or higher harmonic frequencies of the cantilever. This can be done for one or more cantilevers and be repeated in order to determine a shift or change of either of these frequencies as consequence of a process occurring at the cantilever surface. Measuring the frequency shift allows e.g. to determine additional mass adsorbed by the cantilever or a change in the spring constant of the cantilever.

The frequency curve allows determining additional quantities, such as the quality factor or the damping of the cantilever oscillation. For instance, the quality factor Q can be calculated from the resonance frequency (center of a peak) and the bandwidth (width of the peak at a height corresponding to the amplitude divided by the square root of 2).

Comparing the excitation signal to the cantilever signal further allows determining the phase.

In another operation mode the resonance frequency and/or one and/or several higher harmonic frequencies are selected and the shift of this frequency or frequencies is monitored as a function of time, e.g. by means of a phase locked loop (PLL). In this mode, a PLL control loop tracks the frequency by setting the excitation frequency to a value, which keeps the phase difference between excitation signal and cantilever signal at a constant value. The frequency shift of the cantilever is directly determined by measuring the shift of the excitation frequency, which is needed to keep the phase difference constant.

In a preferred operation mode, frequency shifts of multiple cantilevers are readout sequentially, i.e. in time-multiplexed mode, using a PLL. In order to allow high sampling rates, the lock-in time of the PLL has to be kept very small. This can be achieved by saving the current status of the PLL (e.g. state of the feedback parameters and/or filter parameters) for each cantilever at the end of the detection cycle for that particular cantilever. At the beginning of the next detection cycle of the same cantilever, the previous status of the PLL is restored. This drastically reduces the lock-in time of the PLL and allows higher sampling rates. Furthermore, if large resonance frequency shifts are expected to occur between measurement cycles, i.e. during the read-out of other cantilevers, instead of leaving the center frequency of the PLL at its initial (constant) value, the center frequency can be adjusted to the last frequency value obtained for a certain cantilever at the end of the last measurement cycle. The value would be stored as an additional parameter of the PLL status and used as the new center frequency in the next measurement cycle. This method allows for very big lock ranges. Additionally, if this is not sufficient to keep the PLL locked-in, a "look-ahead" algorithm could be implemented calculating the expected new frequency from previously measured frequency shifts and adjusting the center frequency of the PLL accordingly at the beginning of the measurement cycle for a particular cantilever. In its easiest form, the frequency shift measured between the two previous cycles can be added to the center frequency used for the previous measurement cycle, or more sophisticated calculations can be used.

Measuring the frequency shift of a cantilever allows e.g. the determination of changes in the mass load on the cantilever surface (e.g. caused by adsorption or desorption of molecules), the analysis of time-dependent changes of the spring constant of the cantilever (e.g. caused by a structural or conformational change of the chemical surface coating), or the determination of changes in the physical properties of the surrounding affecting the cantilever oscillation (e.g. caused by changes in the viscosity of the surrounding liquid).

The frequency shift from the initial frequency can be measured continuously or repeatedly after defined intervals of time.

In an additional operation mode, corresponding electronics keeps the amplitude of the cantilever constant and the energy needed to maintain the amplitude is measured. This quantity can be used e.g. to determine the damping of the cantilever oscillation and thereby e.g. measure the viscosity of the surrounding liquid.

In a preferred operation mode, the static deflection of the cantilever is read-out in parallel to the oscillation frequency (or frequencies), e.g. by measuring the low-pass-filtered signal of the cantilever.

All operation modes can be used for one or more cantilevers or for cantilever arrays. If more than one cantilever is used, they can either be identical or have different mechanical properties and consequently eigenfrequencies due to e.g. variations in geometry and/or material.

If more than one cantilever is used, their frequencies and frequency shifts can be measured simultaneously or at different points in time (i.e. through time multiplexing).

When using multiple cantilevers, the setup for the oscillation excitation can be designed such that all cantilevers are excited by the same device. Alternatively, each cantilever can be provided with its own device for oscillation excitation.

In the preferred embodiment of the invention, the device according to this invention is integrated into a measurement cell—either directly or by means of a suitable holder as described above—and/or combined with a detection system to read-out cantilever motions (deflection, oscillating frequency). In the preferred embodiment, the cantilever motion is read-out optically, more specifically by the deflection of a laser beam. Hereby, a laser beam is focused on the apex of the cantilever and reflected onto a detector, which can determine the position of the laser beam with high accuracy. When more than one cantilever or a cantilever array is used, multiple light sources and detectors can be used, or multiple light sources can be combined with one detector. In the latter case, the light sources can be switched on and off sequentially, thereby allowing sequential measurement of individual cantilever signals (time-multiplexing). Additional optical elements e.g. for focusing or directing the light beam may be present. Similarly, a moving light source or movable optics can be combined with a detector, whereby the light beams scans over the individual cantilevers and their signals are determined sequentially.

An arrangement of multiple cantilevers allows e.g. the parallel detection of different substances, the use of reference cantilever sensors in order to enhance the reliability of the measurement, or averaging over signal from multiple cantilever sensors in order to increase the signal to noise ratio of the measurement.

In other embodiments, the motion of the cantilever or cantilevers can be measured interferometrically or by means of an electrical signal generated by the cantilever, e.g. when a piezoresistive cantilever is used.

Typically the setup described herein is used to determine mass changes on the cantilever or cantilevers. This can be used to quantitatively detect e.g. biomolecules such as DNA, proteins, active ingredients etc. in liquids. Hereby the cantilevers would be coated (functionalized) with different receptor molecules, each of which is selected to match a certain substance to be detected. In addition, the setup can equally well be used for the detection of micro organisms, viruses or to analyze reactions in cells or chemical processes and interactions.

If the sensor coatings are only partially specific, the combination of differently coated sensors in an array with suitable software (e.g. artificial neural networks, principal component analysis software) allows building an "electronic nose" or "electronic tongue".

Time-resolved measurements allow determining additional quantities such as binding constants, association or dissociation parameters, or constants governing surface layer formation or structural changes.

Furthermore, the setup according to the invention may be used to determine material properties. Examples are the analysis of stiffness or conformational changes of layers deposited on the cantilever or the determination of the viscosity or viscoelastic properties of liquids surrounding the cantilever by observing the oscillation behavior of the cantilever in one of the ways described above.

Further embodiments of the apparatus and methods according to this invention can be drawn from the following descriptions and the appended claims.

DESCRIPTION OF THE DRAWINGS AND EMBODIMENTS

Figure 2:
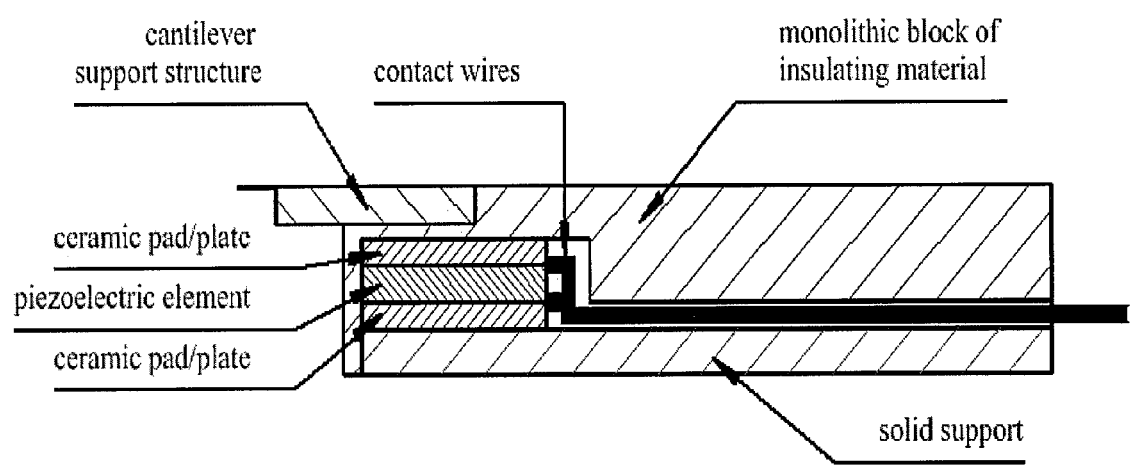
Figure 3:
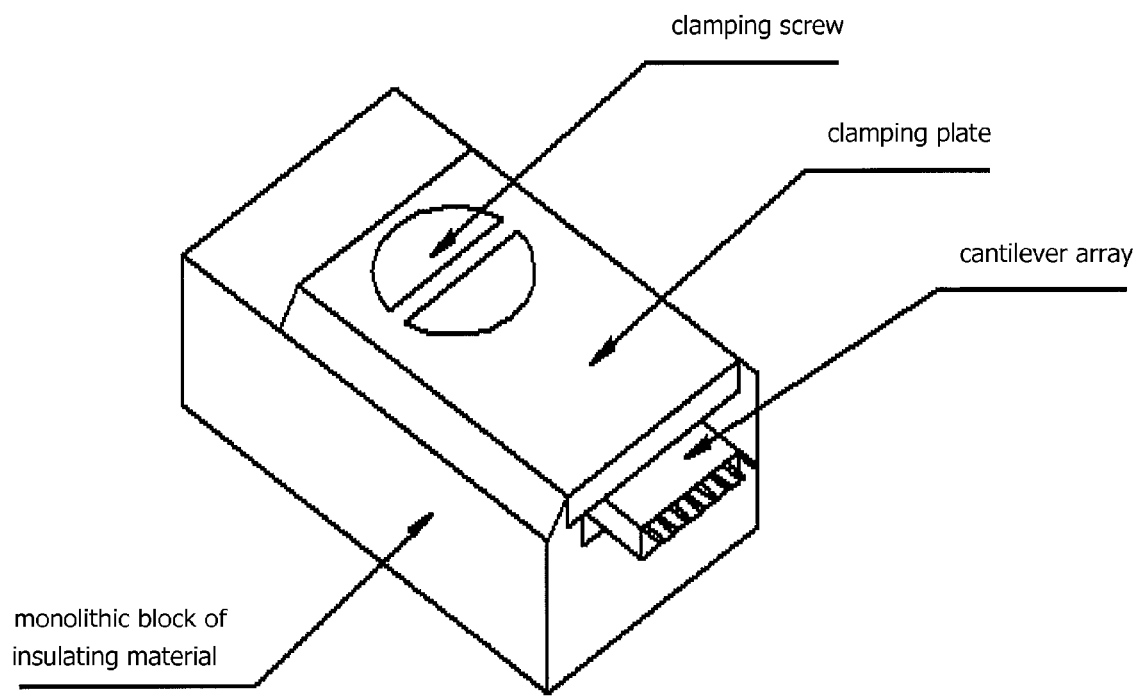
Figure 4:
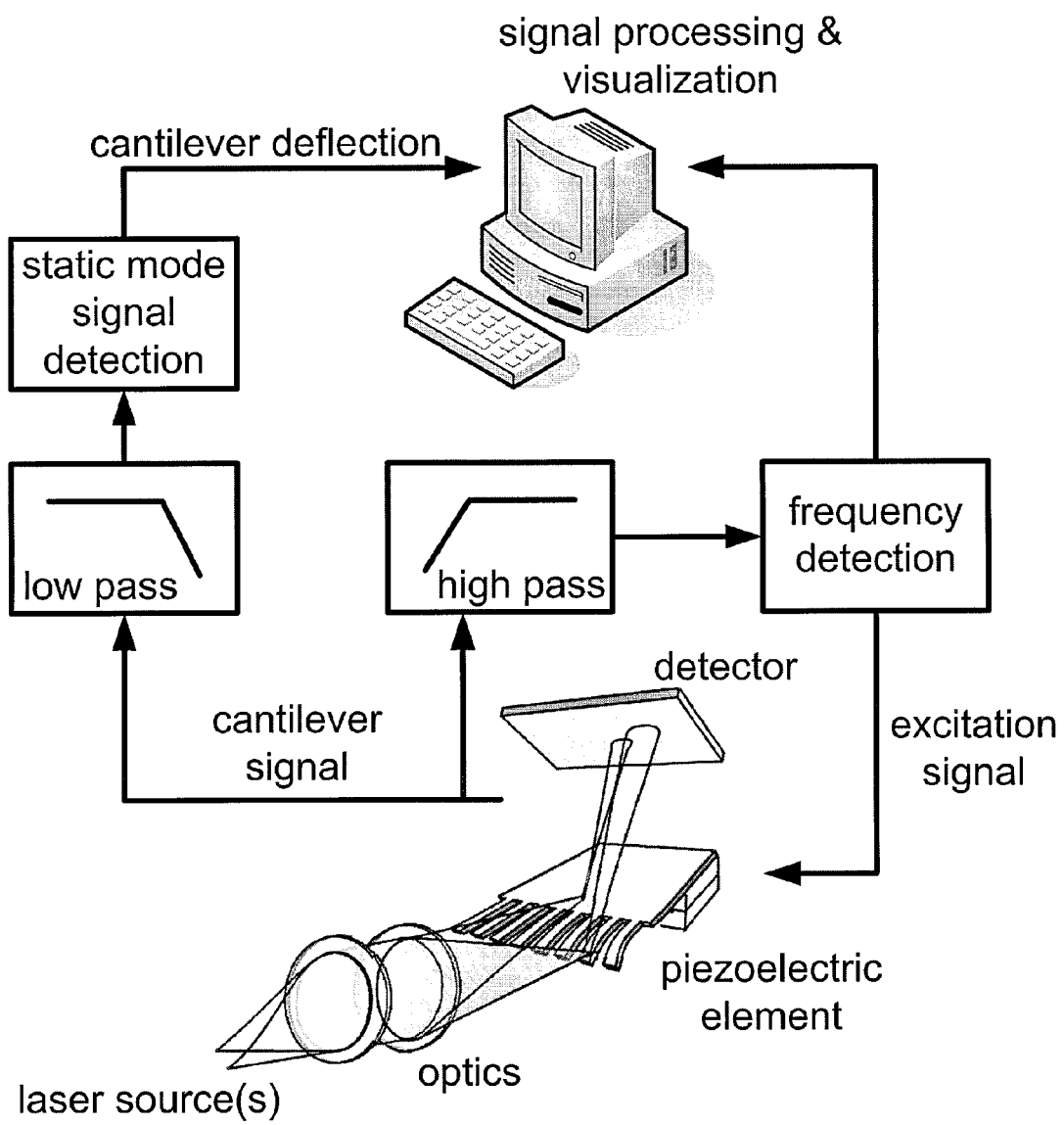
Figure 5:
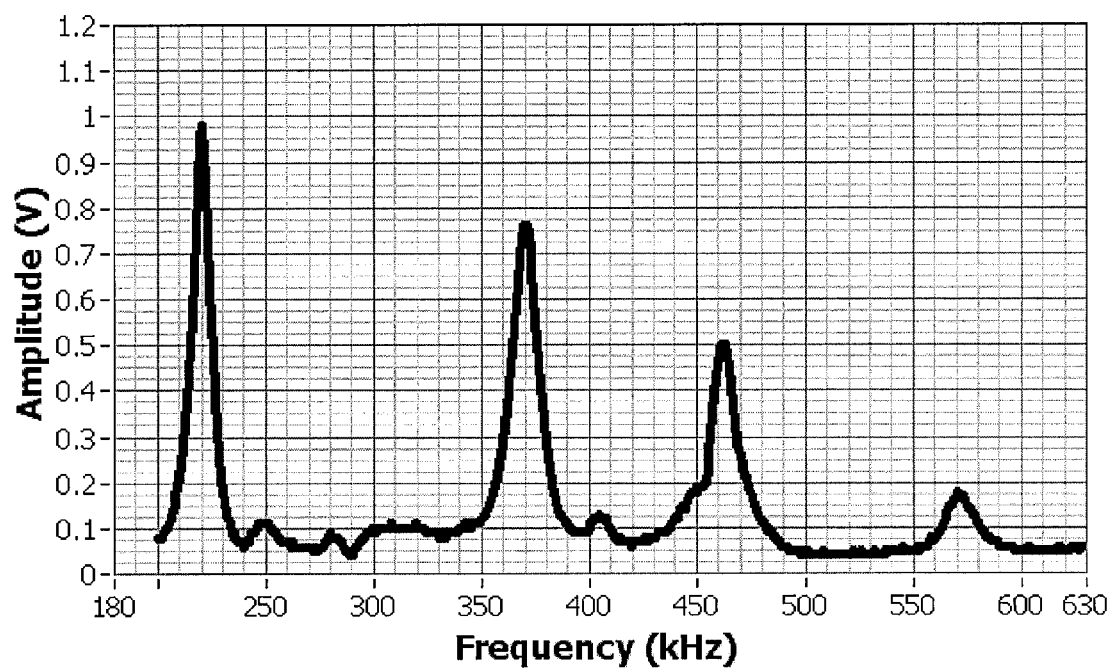
Figure 6:
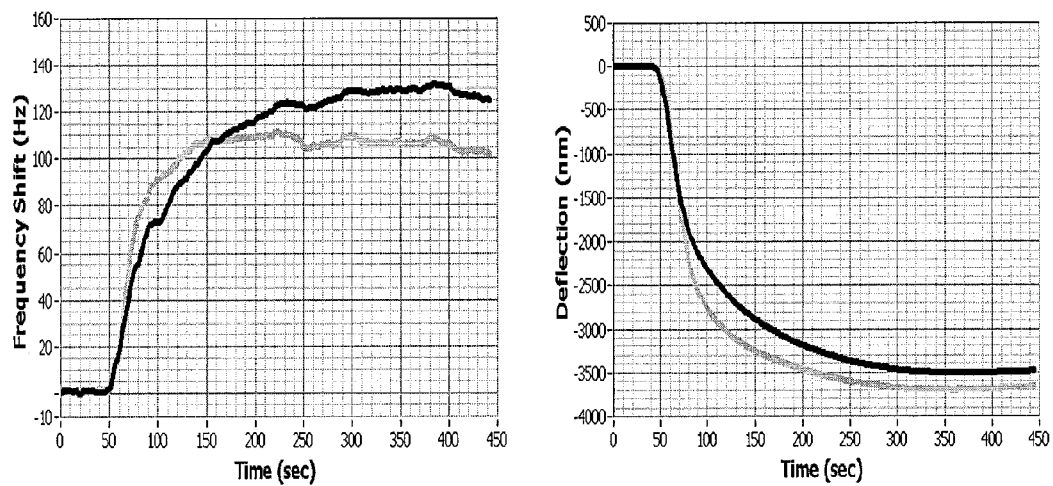
Figure 7:
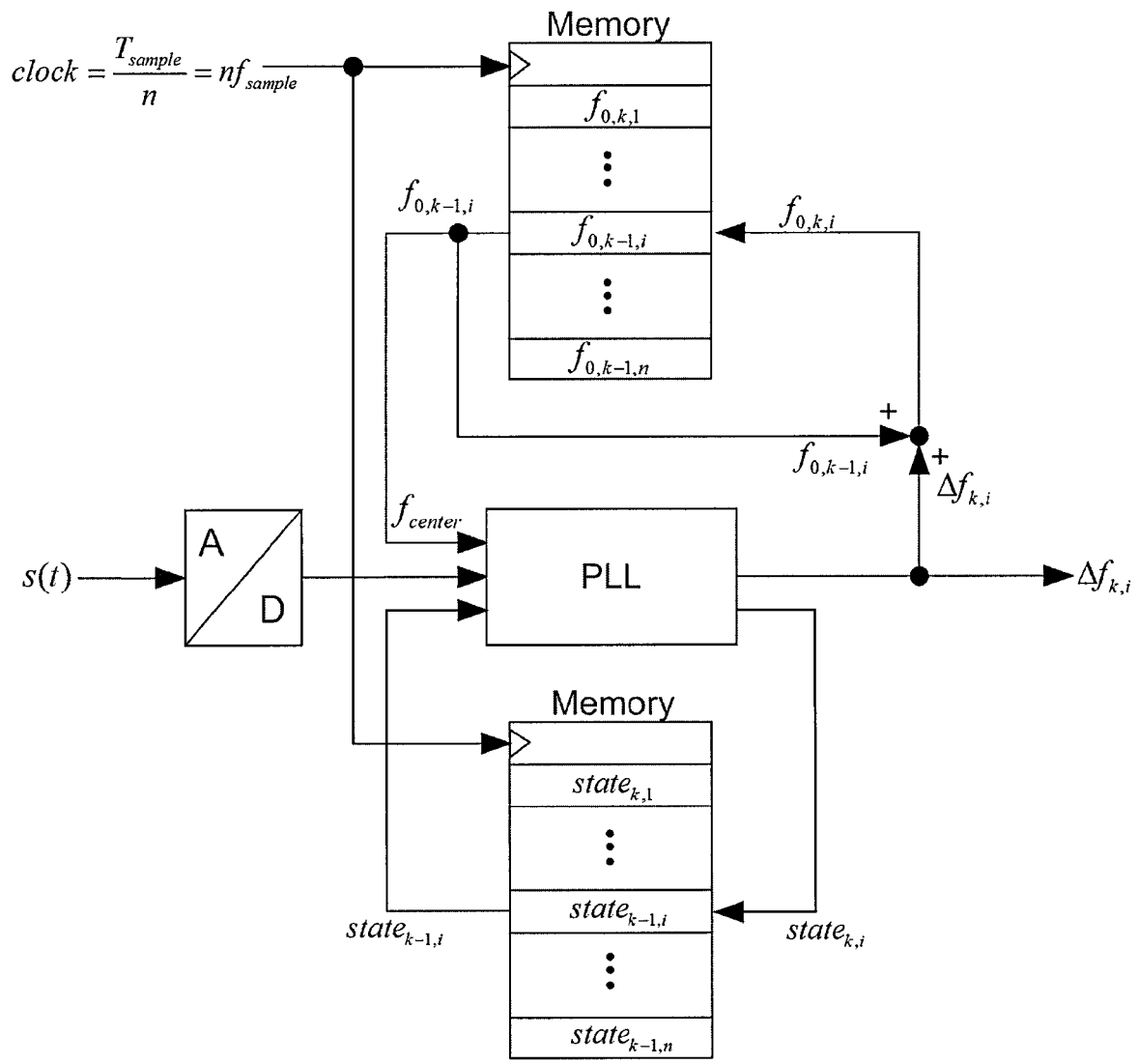
Figure 8:
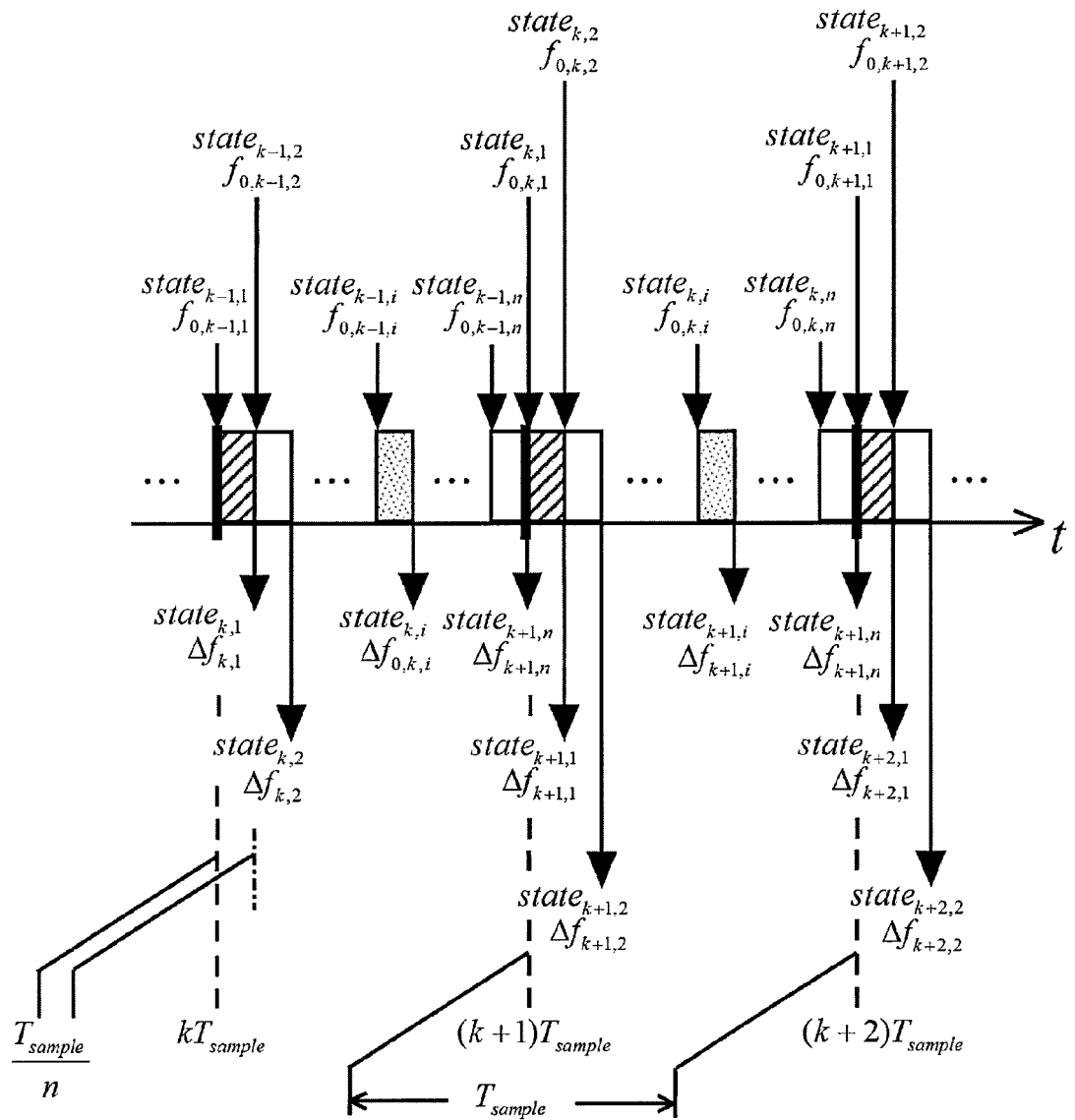

One example of a particular, preferred embodiment of the invention will be described in more detail on the basis of the following figures. They show in FIG. 1 a schematic structure of the device according to this invention;

FIG. 2 a special combination of the device according to this invention with a cantilever holder;

FIG. 3 a particular design of a cantilever holder according to this invention with an exchangeable cantilever array;

FIG. 4 a block diagram of different elements of a full setup, in which the device according to this invention is used;

FIG. 5 a frequency sweep obtained with a setup according to this invention;

FIG. 6 a time-resolved cantilever sensor data illustrating the simultaneous tracking of resonance frequency changes (dynamic operation mode) and cantilever deflection (static operation mode);

FIG. 7 a block diagram illustrating the working principle of a frequency detection circuit for multiple cantilevers according to this invention; and FIG. 8 a scheme of the chronological sequence of a frequency detection algorithm for multiple cantilevers according to this invention.

FIG. 1 shows a schematic cross section of a device for exciting cantilever sensor oscillations according to this invention. Here, a piezoelectric element is the central element used for driving the oscillation. A strong, solid basis/support is located below the piezoelectric element. The piezoelectric element is rigidly fixed to this basis. If the basis is made from an electrically conducting material (e.g. a metal), an insulator is mounted between the piezoelectric element and the basis (e.g. a ceramic pad or plate). A thin insulator, which provides the mechanical coupling to the cantilever (not shown in FIG. 1) is located on the top side of the piezoelectric element. The support structure of the cantilever is typically mounted in the cavity shown in FIG. 1, which provides a flat and smooth contact area for the cantilever support structure. The cantilever can either be permanently attached to the insulator or be pressed into the cavity e.g. by means of a clamping mechanism or a screw. The sides of the piezoelectric elements are also electrically isolated and sealed against intrusion of liquids.

FIG. 2 shows a more special implementation, where the device for exciting the cantilever oscillations is embedded into a cantilever holder. Here, ceramic pads or plates are firmly and permanently attached to the top and bottom side of the piezoelectric element. This sandwich-like structure is firmly and permanently attached to a solid and rigid support, e.g. a metal plate made from titanium. A monolithic block made of an isolating material combines the thin insulating layer which is coupled to the piezoelectric element and accommodates the cantilever, with the isolation against intrusion of liquids. The support structure of the cantilever is used to attach the cantilever either permanently or exchangeably— e.g. by means of a clamping mechanism—to the holder. The support structure of the cantilever can be located exactly above the piezoelectric element (as shown in FIG. 2) or in a shifted position.

FIG. 3 shows a cantilever array holder where the device for exciting the cantilever oscillation is placed inside a monolithic block made of isolating material. The block contains a notch for accommodating a cantilever array. The cantilever array is fixed inside the notch by a clamping plate which presses the cantilever support structure firmly against the holder. The clamping plate itself is fixed with a screw. The clamping plate as well as the screw can be made of a biocompatible material such as PEEK or titanium. This arrangement allows fast and easy exchange of the cantilever array.

FIG. 4 is a block diagram illustrating the various components of a setup according to this invention. Electrical signals are generated by the cantilever or the cantilevers of a cantilever array, respectively, by deflection of one or more laser beams which are used to determine the current deflection of the cantilever or cantilevers. A frequency detector is provided with the high-pass filtered signal. The frequency detector determines the eigenfrequency and/or harmonics and/or the frequency shift as compared to a defined initial frequency. The frequency detector can e.g. be based on a PLL (phase locked loop). The low-pass filtered signal can be determined simultaneously and be used to measure the static deflection of the cantilever. A computer equipped with corresponding software is used to visualize and further process the signals and data.

FIG. 5 shows the frequency spectrum of a single cantilever between 180 kHz and 640 kHz in a liquid, here distilled water. The peaks correspond to higher harmonic oscillation frequencies of the cantilever. The cantilever used for this measurement is 100 micrometers wide, has a length of 500 micrometers, and a thickness of 1 micrometer. The ground frequency in air is slightly below 5 kHz.

The left part of FIG. 6 shows the frequency shift of a cantilever oscillating in a liquid upon adsorption of thiols (mercaptohexanole) on the gold-coated surface of the silicon cantilever. The frequency shift from the initial frequency is tracked by a PLL and plotted as a function of time. Binding of the molecules to the cantilever starts at 50 s and leads to an increase of the cantilever oscillation frequency by 100-120 Hz. The frequency shift is caused by a change of the surface structure of the cantilever, here a formation of a thiol layer, which increases the spring constant of the cantilever. Data is shown for two cantilevers within an array. The right part of FIG. 6 shows the simultaneously acquired, low-pass filtered signal which corresponds to the static deflection of the cantilever as a function of time. The deflection or bending is a consequence of the surface stress which is generated by the adsorption of thiols.

FIG. 7 shows the block diagram of a system or an algorithm for determining resonance frequencies of multiple cantilevers by means of a PLL (phase-locked loop) in a time-multiplexed fashion. At a certain point in time within a current acquisition cycle k, only one cantilever, cantilever i, is active and generates the signal s(t). This signal is then fed into a PLL. Beside the input s(t), the PLL has two more inputs:

state$_{k-1,i}$ is a set of parameters defining the state of the PLL at the end of the previous cycle k−1, when cantilever i was read out the last time. This includes e.g. filter and/or feedback parameters needed to define the state of the PLL.

f$_{center}$ is the center frequency of the PLL, i.e. the frequency which the frequency of s(t) is compared to. This frequency is equal to the resonance frequency f$_{0,k-1,i}$ determined for cantilever i at the end of the previous acquisition cycle k−1.

The end of each acquisition period or cycle for a particular cantilever is determined by the clock signal. At the end of the acquisition period of cantilever i, the frequency shift $\Delta f_{k,i}$, i.e. the difference of the frequency of cantilever i from the center frequency f$_{center}$ in the current acquisition cycle k, is determined and fed e.g. to a computer for storage and/or visualization. In addition, the set of state parameters state$_{k-1,i}$ is overwritten with the current state parameters of the PLL for cantilever i (state$_{k,i}$). Furthermore, the current resonance frequency of cantilever i is calculated by adding the frequency shift $\Delta f_{k,i}$ to the "old" resonance frequency f$_{0,k-1,i}$. This value f$_{0,k-1,i}$ is then overwritten with the value of the current resonance frequency f$_{0,k,i}$ which is to be used as the new center frequency the next time cantilever i is read out. This process is repeated for all n cantilevers, which constitutes and completes a full acquisition cycle. Once acquisition cycle k is finished, the same process is repeated for acquisition cycle k+1 and so on.

If no values for the center frequency and/or PLL state are present from the previous acquisition cycle, e.g. at the beginning of a measurement, default values or values obtained by determining the resonance frequency of each cantilever in a different way can be used.

FIG. 8 illustrates the chronological sequence of events during the time-multiplexed frequency detection of multiple cantilevers using a PLL as illustrated in FIG. 7. The sequence starts with the $k^{th}$ acquisition cycle $kT_{sample}$. During the sample cycle, the frequency is determined for each of n cantilevers, starting with cantilever i=1 and ending with cantilever i=n, according to the following scheme:

1. The parameters stored for cantilever i during the last acquisition cycle $(k-1)T_{sample}$ are restored. This includes e.g. PLL state parameters $state_{k-1,i}$ and resonance frequency $f_{0,k-1,i}$.
2. After the acquisition period $T_{sample}/n$ needed to measure the frequency shift $\Delta f_{k,i}$, the new state parameters of the PLL $state_{k,i}$ are stored. Additionally, the new resonance frequency $f_{k,i}=f_{k-1,i}+\Delta f_{k,i}$ is calculated and stored for use in the next acquisition cycle.

After this has been done for all cantilevers, a new acquisition cycle k+1 starts. The acquisition cycle can be repeated an arbitrary number of times.

The measurement functions described above can easily be implemented by a person skilled in the art. Where commercial software is unavailable, applicable software can easily be implemented by someone skilled in the art.

The invention claimed is:

1. A system for generating oscillations of at least one micromechanical cantilever with a mechanical oscillator, wherein
    said oscillator is electrically insulated,
    said oscillator is contained in a package which is gas-tight or liquid-tight, respectively,
    a first side of said oscillator is firmly attached to a rigid support which is essentially incapable of oscillating,
    a second, opposite side of said oscillator includes an insulating layer to which said at least one cantilever is affixed, and
    a frequency detector is provided for determining an eigenfrequency and/or a harmonic of a micromechanical cantilever by exciting a cantilever oscillation at or near its eigenfrequency and/or harmonics.

2. The system according to claim 1, wherein the oscillator is a piezoelectric element, said piezoelectric element being fixed to the rigid support with a rear side and having a front side covered with the insulating layer.

3. The system according to claim 2, further comprising ceramic plates attached to at least two sides of the piezoelectric element, which plates are in firm contact with the rigid support and the insulating layer, respectively.

4. The system according to claim 1, wherein the rigid support is made of a metal.

5. The system according to claim 1, wherein the insulating layer is made of a biocompatible material.

6. The system according to claim 1, wherein the oscillator includes a fixture on the insulating layer, said fixture serving for detachably affixing said at least one micromechanical cantilever.

7. The system according to claim 5, wherein the biocompatible material includes PEEK.

8. The system according to claim 1, further comprising a first electronic circuit connected to the oscillator, said first circuit generating an electrical signal driving the oscillator to oscillate at various frequencies.

9. The system according to claim 1, further comprising a second electronic circuit for evaluating a signal derived from an oscillation of a cantilever, said second circuit including a low pass filter whose output signal is used to determine a deflection of said cantilever and including a high pass filter whose output signal is used to determine an oscillation frequency of said cantilever.

10. The system according to claim 9, further comprising a feedback circuit generating an excitation signal derived from the output of the high pass filter indicating the oscillation frequency of said cantilever and feeding said excitation signal back to the oscillator.

11. The system according to claim 9, further comprising PLL means (phase-locked loop means) for determining a resonance frequency of each cantilever i of a plurality of cantilevers by time-multiplexing, said PLL means including:
    an input for receiving a signal s(t) generated by said cantilever i when it is active,
    a memory for storing a first set of parameters, $state_{k-1,i}$, defining the state of the PLL at the end of a first acquisition cycle k−1, said first set of parameters corresponding to said signals s(t) of said cantilever i received during said first acquisition cycle k−1 and including a value for the resonance frequency, $f_{0,k-1,i}$, of said cantilever i,
    a memory for storing a second set of parameters, $state_{k,i}$, defining the state of the PLL at the end of a second acquisition cycle k, said second set of parameters corresponding to said signals s(t) of said cantilever i received during said second acquisition cycle k−1,
    means for determining a frequency shift $\Delta f_{k,i}$ defined as the difference between said value for the resonance frequency, $f_{0,k-1,i}$, of said cantilever i in said first acquisition cycle k−1 and said value for the resonance frequency, $f_{0,k,i}$, of said cantilever i in said second acquisition cycle k,
    means for storing and/or visualizing said frequency shift $\Delta f_{k,i}$.

12. The system according to claim 1, further comprising
    means for producing a frequency sweep over a given frequency range to be applied to the cantilever and
    means for measuring a frequency-dependence of an amplitude of said cantilever to determine an eigenfrequency of said cantilever.

13. The system according to claim 1, further comprising
    means for keeping an oscillation amplitude of the cantilever constant and
    means for measuring an energy necessary to be provided to the oscillator for this purpose.

14. The system according to claim 1, further comprising means for simultaneously measuring a static deflection of at least two cantilevers.

15. The system according to claim 1, wherein the insulating layer is thin.

16. The system according to claim 2, wherein the piezoelectric element is a dither piezo.

17. The system according to claim 4, wherein the rigid support is made of a hard metal.

* * * * *